United States Patent
Gellman

(10) Patent No.: US 8,328,877 B2
(45) Date of Patent: Dec. 11, 2012

(54) STENT RETENTION ELEMENT AND RELATED METHODS

(75) Inventor: Barry N. Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1841 days.

(21) Appl. No.: 10/100,993

(22) Filed: Mar. 19, 2002

(65) Prior Publication Data

US 2003/0181842 A1 Sep. 25, 2003

(51) Int. Cl.
*A61F 2/04* (2006.01)
(52) U.S. Cl. .......................... 623/23.66; 604/8
(58) Field of Classification Search ................... 606/108, 606/113, 200, 153–156, 215, 216, 127; 623/23.69, 623/23.7, 1.22, 23.64–23.66; 604/8, 544, 604/317, 324
See application file for complete search history.

(56) References Cited

U.S. PATENT DOCUMENTS

| | | |
|---|---|---|
| 2,002,559 A | 5/1935 | Wappler |
| 2,583,937 A | 1/1952 | Fossati |
| 3,176,114 A | 3/1965 | Kneisley |
| 3,860,006 A | 1/1975 | Patel |
| 3,890,977 A | 6/1975 | Wilson |
| 3,920,023 A | 11/1975 | Dye et al. |
| 3,946,741 A | 3/1976 | Adair |
| 4,046,150 A | 9/1977 | Schwartz et al. |
| 4,212,304 A | 7/1980 | Finney |
| 4,233,493 A | 11/1980 | Nath |
| 4,289,966 A | 9/1981 | Roberts |
| 4,295,464 A | 10/1981 | Shihata |
| 4,307,723 A | 12/1981 | Finney |
| 4,334,327 A | 6/1982 | Lyman et al. |
| 4,340,307 A | 7/1982 | Diamond et al. |
| 4,368,730 A | 1/1983 | Sharrock |
| 4,405,314 A | 9/1983 | Cope |
| 4,419,094 A | 12/1983 | Patel |
| 4,472,728 A | 9/1984 | Grant et al. |
| 4,509,517 A | 4/1985 | Zibelin |
| 4,531,933 A * | 7/1985 | Norton et al. ..................... 604/8 |
| 4,541,272 A | 9/1985 | Bause |
| 4,548,505 A | 10/1985 | Ono |
| 4,553,542 A | 11/1985 | Schenck et al. |
| 4,560,286 A | 12/1985 | Wickersheim |
| 4,568,338 A | 2/1986 | Todd |
| 4,589,868 A | 5/1986 | Dretler |
| 4,590,938 A | 5/1986 | Segura et al. |

(Continued)

FOREIGN PATENT DOCUMENTS

AU 712420 2/2000

(Continued)

OTHER PUBLICATIONS

International Search Report in PCT/US03/07413 dated Jun. 27, 2003.

(Continued)

*Primary Examiner* — Tuan V Nguyen
*Assistant Examiner* — Thomas McEvoy

(57) ABSTRACT

In one embodiment, the invention is directed to a stent retention element having an elastic member adapted to be incorporated with a first end of an elongate stent and to coil toward a second end of the elongate stent to anchor the elongate stent at an anatomical site. According to one feature, the stent retention element expands and compresses to effectively lengthen and shorten, respectively, the stent to accommodate ureter lengthening and shortening.

38 Claims, 9 Drawing Sheets

U.S. PATENT DOCUMENTS

| | | | |
|---|---|---|---|
| 4,610,657 A | 9/1986 | Densow | |
| 4,625,726 A | 12/1986 | Duthoy | |
| 4,643,716 A | 2/1987 | Drach | |
| 4,655,771 A | 4/1987 | Wallsten | |
| 4,671,795 A | 6/1987 | Mulchin | |
| 4,672,972 A | 6/1987 | Berke | |
| 4,694,838 A | 9/1987 | Wijayarthna et al. | |
| 4,699,611 A | 10/1987 | Bowden | |
| 4,706,671 A * | 11/1987 | Weinrib | 606/159 |
| 4,713,049 A | 12/1987 | Carter | |
| 4,718,417 A | 1/1988 | Kittrell et al. | |
| 4,732,152 A | 3/1988 | Wallsten et al. | |
| 4,738,667 A * | 4/1988 | Galloway | 604/530 |
| 4,747,840 A | 5/1988 | Ladika et al. | |
| 4,762,128 A | 8/1988 | Rosenbluth | |
| 4,785,059 A | 11/1988 | Fydelor et al. | |
| 4,787,884 A | 11/1988 | Goldberg | |
| 4,790,809 A | 12/1988 | Kuntz | |
| 4,790,810 A * | 12/1988 | Pugh et al. | 604/544 |
| 4,790,816 A | 12/1988 | Sundblom et al. | |
| 4,807,626 A | 2/1989 | McGirr | |
| 4,813,790 A | 3/1989 | Frankel et al. | |
| 4,813,925 A | 3/1989 | Anderson, Jr. et al. | |
| 4,820,262 A | 4/1989 | Finney | |
| 4,846,814 A | 7/1989 | Ruiz | |
| 4,872,458 A | 10/1989 | Kanehira et al. | |
| 4,874,360 A | 10/1989 | Goldberg et al. | |
| 4,882,623 A | 11/1989 | Uchikubo | |
| 4,887,996 A | 12/1989 | Bengmark | |
| 4,893,623 A | 1/1990 | Rosenbluth | |
| 4,895,156 A | 1/1990 | Schulze | |
| 4,902,896 A | 2/1990 | Fertig, Sr. et al. | |
| 4,913,683 A | 4/1990 | Gregory | |
| 4,927,426 A | 5/1990 | Dretler | |
| 4,928,172 A | 5/1990 | Uehara et al. | |
| 4,931,037 A | 6/1990 | Wetterman | |
| 4,938,602 A | 7/1990 | May et al. | |
| 4,950,228 A | 8/1990 | Knapp, Jr. et al. | |
| 4,954,126 A | 9/1990 | Wallsten | |
| 4,957,475 A | 9/1990 | Kreill | |
| 4,957,479 A | 9/1990 | Roemer | |
| 4,973,301 A | 11/1990 | Nissenkorn | |
| 4,978,341 A | 12/1990 | Niederhauser | |
| 4,981,138 A | 1/1991 | Deckelbaum et al. | |
| 4,986,814 A | 1/1991 | Burney et al. | |
| 4,990,133 A | 2/1991 | Solazzo | |
| 4,990,228 A | 2/1991 | Perusich et al. | |
| 5,001,556 A | 3/1991 | Nakamura et al. | |
| 5,009,655 A | 4/1991 | Daignault, Jr. et al. | |
| 5,011,469 A | 4/1991 | Buckberg et al. | |
| 5,019,102 A | 5/1991 | Hoene | |
| 5,021,888 A | 6/1991 | Kondou et al. | |
| 5,026,377 A | 6/1991 | Burton et al. | |
| 5,042,494 A | 8/1991 | Alfano | |
| 5,045,056 A | 9/1991 | Behl | |
| 5,052,998 A | 10/1991 | Zimmon | |
| 5,056,503 A | 10/1991 | Nagasaki et al. | |
| 5,061,275 A | 10/1991 | Wallsten et al. | |
| 5,078,684 A | 1/1992 | Yasuda | |
| 5,078,720 A | 1/1992 | Burton et al. | |
| 5,078,736 A | 1/1992 | Behl | |
| 5,085,629 A | 2/1992 | Goldberg et al. | |
| 5,116,309 A | 5/1992 | Coll | |
| 5,116,759 A | 5/1992 | Klainer et al. | |
| 5,129,910 A | 7/1992 | Phan et al. | |
| 5,141,502 A | 8/1992 | Macaluso, Jr. | |
| 5,147,370 A | 9/1992 | McNamara et al. | |
| 5,159,920 A | 11/1992 | Condon et al. | |
| 5,171,233 A | 12/1992 | Amplatz et al. | |
| 5,176,625 A | 1/1993 | Brisson | |
| 5,176,626 A | 1/1993 | Soehendra | |
| 5,187,572 A | 2/1993 | Nakamura et al. | |
| 5,206,174 A | 4/1993 | Gehrke et al. | |
| 5,221,253 A | 6/1993 | Coll | |
| 5,224,953 A | 7/1993 | Morgentaler | |
| 5,233,621 A | 8/1993 | Lawandy | |
| 5,234,456 A | 8/1993 | Silvestrini | |
| 5,242,437 A | 9/1993 | Everett et al. | |
| 5,246,445 A | 9/1993 | Yachia et al. | |
| 5,246,447 A | 9/1993 | Rosen et al. | |
| 5,262,645 A | 11/1993 | Lambert et al. | |
| 5,269,802 A | 12/1993 | Garber | |
| 5,282,784 A | 2/1994 | Willard | |
| 5,295,954 A | 3/1994 | Sachse | |
| 5,304,214 A | 4/1994 | DeFord et al. | |
| 5,309,907 A | 5/1994 | Fang et al. | |
| 5,311,858 A | 5/1994 | Adair | |
| 5,318,024 A | 6/1994 | Kittrell et al. | |
| 5,330,482 A | 7/1994 | Gibbs et al. | |
| 5,334,185 A | 8/1994 | Giesy et al. | |
| 5,342,387 A | 8/1994 | Summers | |
| 5,346,467 A | 9/1994 | Coll | |
| 5,351,532 A | 10/1994 | Hager | |
| 5,354,263 A | 10/1994 | Coll | |
| 5,354,309 A | 10/1994 | Schnepp-Pesch et al. | |
| 5,356,423 A | 10/1994 | Tihon et al. | |
| 5,364,340 A | 11/1994 | Coll | |
| 5,372,600 A | 12/1994 | Beyar et al. | |
| 5,377,676 A | 1/1995 | Vari et al. | |
| 5,383,928 A | 1/1995 | Scott et al. | |
| 5,391,196 A | 2/1995 | Devonec | |
| 5,398,844 A | 3/1995 | Zaslavsky et al. | |
| 5,401,257 A | 3/1995 | Chevalier, Jr. et al. | |
| 5,403,324 A | 4/1995 | Ciervo et al. | |
| 5,405,369 A | 4/1995 | Selman et al. | |
| 5,408,998 A | 4/1995 | Mersch | |
| 5,411,551 A | 5/1995 | Winston et al. | |
| 5,417,207 A | 5/1995 | Young et al. | |
| 5,417,210 A | 5/1995 | Funda et al. | |
| 5,445,608 A | 8/1995 | Chen et al. | |
| 5,461,229 A | 10/1995 | Sauter et al. | |
| 5,466,242 A * | 11/1995 | Mori | 606/198 |
| 5,467,767 A | 11/1995 | Alfano et al. | |
| 5,484,384 A | 1/1996 | Fearnot | |
| 5,486,183 A | 1/1996 | Middleman et al. | |
| 5,496,330 A | 3/1996 | Bates et al. | |
| 5,500,013 A | 3/1996 | Buscemi et al. | |
| 5,514,176 A | 5/1996 | Bosley, Jr. et al. | |
| 5,514,178 A | 5/1996 | Torchio | |
| 5,517,997 A | 5/1996 | Fontenot | |
| 5,520,697 A | 5/1996 | Lindenberg et al. | |
| 5,523,092 A | 6/1996 | Hanson et al. | |
| 5,527,337 A | 6/1996 | Stack et al. | |
| 5,531,716 A | 7/1996 | Luzio et al. | |
| 5,531,735 A | 7/1996 | Thompson | |
| 5,531,741 A | 7/1996 | Barbacci | |
| 5,540,701 A * | 7/1996 | Sharkey et al. | 606/153 |
| 5,540,713 A | 7/1996 | Schnepp-Pesch et al. | |
| 5,542,928 A | 8/1996 | Evans et al. | |
| 5,545,135 A | 8/1996 | Iacobe et al. | |
| 5,545,210 A | 8/1996 | Hess et al. | |
| 5,554,181 A | 9/1996 | Das | |
| 5,556,421 A | 9/1996 | Prutchi et al. | |
| 5,562,641 A | 10/1996 | Flomenbilt et al. | |
| 5,571,152 A | 11/1996 | Chen et al. | |
| 5,599,291 A | 2/1997 | Balbierz et al. | |
| 5,601,572 A | 2/1997 | Middleman et al. | |
| 5,609,629 A | 3/1997 | Fearnot et al. | |
| 5,626,139 A | 5/1997 | Szeles et al. | |
| 5,632,746 A | 5/1997 | Middleman et al. | |
| 5,639,278 A | 6/1997 | Dereume et al. | |
| 5,647,368 A | 7/1997 | Zeng et al. | |
| 5,647,843 A * | 7/1997 | Mesrobian et al. | 604/8 |
| 5,650,116 A | 7/1997 | Thompson | |
| 5,653,689 A | 8/1997 | Buelna et al. | |
| 5,667,486 A | 9/1997 | Mikulich et al. | |
| 5,674,277 A | 10/1997 | Freitag | |
| 5,676,697 A | 10/1997 | McDonald | |
| 5,681,274 A | 10/1997 | Perkins et al. | |
| 5,684,051 A | 11/1997 | Thompson | |
| 5,693,069 A | 12/1997 | Shallman | |
| 5,693,083 A | 12/1997 | Baker et al. | |
| 5,697,936 A | 12/1997 | Shipko et al. | |
| 5,707,386 A | 1/1998 | Schnepp-Pesch et al. | |
| 5,707,387 A | 1/1998 | Wijay | |
| 5,709,874 A | 1/1998 | Hanson et al. | |
| 5,716,393 A | 2/1998 | Lindenberg et al. | |

| | | |
|---|---|---|
| 5,718,862 A | 2/1998 | Thompson |
| 5,720,754 A | 2/1998 | Middleman et al. |
| 5,728,122 A | 3/1998 | Leschinsky et al. |
| 5,730,134 A | 3/1998 | Dumoulin et al. |
| 5,746,766 A | 5/1998 | Edoga |
| 5,749,879 A | 5/1998 | Middleman et al. |
| 5,762,071 A | 6/1998 | Newman et al. |
| 5,766,209 A | 6/1998 | Devonec |
| 5,776,161 A | 7/1998 | Globerman |
| 5,776,348 A | 7/1998 | Selengut et al. |
| 5,779,716 A | 7/1998 | Cano et al. |
| 5,792,145 A | 8/1998 | Bates et al. |
| 5,792,400 A | 8/1998 | Talja et al. |
| 5,795,319 A | 8/1998 | Ali |
| 5,800,478 A | 9/1998 | Chen et al. |
| 5,820,628 A | 10/1998 | Middleman et al. |
| 5,830,156 A | 11/1998 | Ali |
| 5,830,179 A | 11/1998 | Mikus et al. |
| 5,843,176 A | 12/1998 | Weier |
| 5,853,421 A | 12/1998 | Leschinsky et al. |
| 5,860,999 A | 1/1999 | Schnepp-Pesch et al. |
| 5,865,815 A | 2/1999 | Tihon |
| 5,871,475 A | 2/1999 | Frassica |
| 5,871,501 A | 2/1999 | Leschinsky et al. |
| 5,876,417 A | 3/1999 | Devonex et al. |
| 5,895,398 A * | 4/1999 | Wensel et al. .................. 606/127 |
| 5,904,690 A | 5/1999 | Middleman et al. |
| 5,906,622 A | 5/1999 | Lippitt et al. |
| 5,906,640 A | 5/1999 | Penn et al. |
| 5,908,435 A | 6/1999 | Samuels |
| 5,921,952 A | 7/1999 | Desmond, III et al. |
| 5,924,175 A | 7/1999 | Lippitt et al. |
| 5,928,217 A | 7/1999 | Mikus et al. |
| 5,944,728 A | 8/1999 | Bates |
| 5,957,900 A | 9/1999 | Ouchi |
| 5,962,007 A | 10/1999 | Cooper et al. |
| 5,964,744 A | 10/1999 | Balbierz et al. |
| 5,964,771 A | 10/1999 | Beyar et al. |
| 5,971,967 A | 10/1999 | Willard |
| 5,971,995 A | 10/1999 | Rousseau |
| 5,989,266 A | 11/1999 | Foster |
| 6,004,330 A | 12/1999 | Middleman et al. |
| 6,019,779 A | 2/2000 | Thorud et al. |
| 6,027,516 A | 2/2000 | Kolobow et al. |
| 6,033,413 A | 3/2000 | Mikus et al. |
| 6,045,568 A | 4/2000 | Igaki et al. |
| 6,053,900 A * | 4/2000 | Brown et al. .................. 604/530 |
| 6,093,196 A | 7/2000 | Okada |
| 6,093,199 A | 7/2000 | Brown et al. |
| 6,096,053 A | 8/2000 | Bates |
| 6,099,506 A | 8/2000 | Macoviak et al. |
| 6,099,534 A | 8/2000 | Bates et al. |
| 6,102,887 A | 8/2000 | Altman |
| 6,113,621 A | 9/2000 | Wiktor |
| 6,123,722 A | 9/2000 | Fogarty et al. |
| 6,136,005 A | 10/2000 | Goode et al. |
| 6,139,536 A | 10/2000 | Mikus et al. |
| 6,152,936 A | 11/2000 | Christy et al. |
| 6,159,220 A | 12/2000 | Gobron et al. |
| 6,159,230 A | 12/2000 | Samuels |
| 6,168,602 B1 | 1/2001 | Ryan |
| 6,168,603 B1 | 1/2001 | Leslie et al. |
| 6,171,338 B1 | 1/2001 | Talja et al. |
| 6,174,305 B1 | 1/2001 | Mikus et al. |
| 6,174,318 B1 | 1/2001 | Bates et al. |
| 6,187,017 B1 | 2/2001 | Gregory, Jr. |
| 6,190,394 B1 | 2/2001 | Lind et al. |
| 6,203,552 B1 | 3/2001 | Bagley et al. |
| 6,214,042 B1 | 4/2001 | Jacobsen et al. |
| 6,258,098 B1 | 7/2001 | Taylor et al. |
| 6,290,721 B1 | 9/2001 | Heath |
| 6,402,736 B1 * | 6/2002 | Brown et al. .................. 604/523 |
| 6,620,202 B2 * | 9/2003 | Bottcher et al. ............. 623/23.7 |
| 6,685,744 B2 * | 2/2004 | Gellman et al. ........... 623/23.66 |
| 6,702,846 B2 * | 3/2004 | Mikus et al. .................. 623/1.22 |
| 2001/0053936 A1 * | 12/2001 | Whitmore, III ............... 623/23.7 |
| 2002/0010481 A1 * | 1/2002 | Jayaraman .................... 606/151 |

FOREIGN PATENT DOCUMENTS

| | | |
|---|---|---|
| EP | 0 806 189 A1 | 11/1997 |
| HU | 214735 | 7/1998 |
| JP | 57-90150 | 6/1982 |
| JP | 01-43917 | 2/1989 |
| JP | 02-223828 | 9/1990 |
| JP | 05-235327 | 10/1993 |
| JP | 06-242233 | 9/1994 |
| JP | 07-88105 | 4/1995 |
| JP | 07-289506 | 11/1995 |
| JP | 08-83569 | 3/1996 |
| JP | 09-192138 | 7/1997 |
| WO | WO 88/05317 | 7/1988 |
| WO | WO 90/04352 | 5/1990 |
| WO | WO 93/13824 | 7/1993 |
| WO | WO 94/13191 | 6/1994 |
| WO | WO 96/05693 | 2/1996 |
| WO | WO 97/01985 | 1/1997 |
| WO | WO 97/27808 | 8/1997 |
| WO | WO 98/25656 | 6/1998 |
| WO | WO 99/16363 | 4/1999 |
| WO | WO 00/66032 | 11/2000 |
| WO | WO 00/71036 | 11/2000 |
| WO | WO 01/01869 | 1/2001 |
| WO | WO 02/15822 A1 | 2/2002 |

OTHER PUBLICATIONS

"IEEE Transactions on Biomedical Engineering" Aug. 1979, vol. BME-26, No. 8.
"Project 4.4: Intergrated UV-Sensor", Final Report 1995.
"Stay Tuned: Photonic Filters Color Your World". Photonis Design and Solutions, Mar. 1997.
Bard Urological Division Product Catalog, 1990.
Cook Urological Product Catalog—Ureteral Stents, 1987.
Cook Urological Product Brochure—Filiform Ureteral Multi-Length Silicone Stent Sets, 1989.
Cook Urological Product Catalog—Urological Surgical Products,1990-1991.
Surgitek Product Brochure—Lubri-Flex Ureteral Stent Kit, "The Solution is Perfectly Clear", 1990.
Bard Product Brochure—Introducing The Bard Urinary Diversion Stent, 1984.
Bard Product Brochure—Stents to Satisfy the Urologist: Figure Four Pigtail, Multi-Length or Specific Length, Silicone or Polyurethane—New Injection Stent, 1988.
Bard/angiomed Product Brochure—Puroflex and Urosoft "Cross Stent" Ureteral Stent Sets and Schuller Ureterotomy Stent Sets, 1988.
Bard Product Brochure—Introducing The Bard Pediatric Urethral Stent, 1983.
Bard Urological Division Specialty Catalog, 1986.
Bard Product Brochure—Coil Stent with Figure Four End, 1985.
Cook Urological Product Catalog, 1995.
Vance Products, Inc. (affiliated with Cook) Product Catalog—Surgical Products, May 12, 1979.
Vance Products, Inc. (affiliated with Cook) Product Catalog—Surgical Products for Urology, May 19, 1980.
Vance Products, Inc. (affiliated with Cook) Product Catalog—Surgical Products for Urology, May 8, 1981.
Vance Products, Inc. (affiliated with Cook) Product Catalog—Urological/Surgical Products, 1982-1983.
Vance Products, Inc. (affiliated with Cook) Product Catalog—Urological/Surgical Products, 1983-1984.
Cook Urological Product Catalog—Urological, Surgical and Endourological Products, 1984-1985.
Cook Urological Product Catalog—Ureteral Catheters, 1986.
Cook Urological Product Catalog—Ureteral Catheters, 1992.
Cook Urological Product Catalog—Stent Spectrum, 1996.
Cook Urological Catalog Supplement, May 1998.
Bard Urological Division Product Catalog, 1998.

* cited by examiner (BACKGROUND)

STENT RETENTION ELEMENT AND RELATED METHODS

TECHNICAL FIELD

This invention generally relates to stents. More particularly, in one embodiment, the invention is directed to a stent retention element.

BACKGROUND OF THE INVENTION

A stent is a medical device adapted for propping open an obstructed passage within the body, such as a blocked ureter. In general, ureteral blockage is a medical condition requiring treatment. A ureteral blockage can occur for a number of reasons, including the passage of a kidney stone and/or other material into the ureter where it becomes entrapped. Also, a tumor growing against the outer wall of the ureter can force compression or constriction of the ureter. A tumor on the internal ureteral wall can also cause blockage of the ureter. Ureteral stents are often used to correct such problems. A ureteral stent may be placed inside the ureter on a temporary basis to allow proper drainage of fluids from the kidney to the urinary bladder. One end of a typical ureteral stent is placed in the kidney and the other end is placed in the urinary bladder. The end positioned in the kidney is typically configured to retain the stent within the renal pelvis and to prevent the downward migration of the stent into the ureter. The bladder end of the stent is typically configured to prevent upward migration of the stent towards the kidney.

FIG. 1 is a conceptual background drawing showing a portion of the human urinary tract. Referring to FIG. 1, in a human urinary tract 100, the ureters 102 and 104 transport urine from the kidneys 106 and 108 to the urinary bladder 110. The trigone region 112 of the urinary bladder 110 is located between the urethral opening 114 and the two ureteral orifices 116 and 118. The pain associated with an in-dwelling ureteral stent is attributable in-part to contact between the stent and the urinary bladder mucosa 120 in the trigone region 112. The trigone region 112 is believed to be particularly innervated and sensitive to the presence of any foreign bodies such as the bladder end of a ureteral stent.

The placement of conventional ureteral stents generally requires a measurement by the physician to ascertain the length of, for example, the ureter 102. Typically, conventional stents include an elongate body at least long enough to traverse the distance in the ureter 102 between the kidney 106 and the urinary bladder 110. Conventional stents also typically include some type of anchor at one or both of the kidney 106 and urinary bladder 116 ends. Such anchors generally consist of a coil formed perpendicular to a stent axis and integrated with one or both of the kidney 106 and urinary bladder 110 ends of the stent. These coils secure the stent to prevent it from migrating in the ureter 102, either upward toward the kidney 106 or downward toward the urinary bladder 110.

One drawback of such conventional stents, is that typically, they need to be of sufficient length to allow for some relative movement between the kidney 106 and the urinary bladder 110, due to, for example, patient movement or peristaltic action, without becoming dislodged. However, such increased stent length can cause the stent to protrude far enough into the kidney 106 and/or the urinary bladder 110 to cause kidney 106 and urinary bladder 110 irritation. The trigone region 112 of the urinary bladder 110 is especially susceptible to such irritation. To further complicate matters, stents having insufficient length may dislodge and migrate in the ureter 102, either toward the kidney 106 or toward the urinary bladder 110.

SUMMARY OF THE INVENTION

Accordingly, an anchoring approach is needed that reduces patient irritation and that does not lend itself to migration. The invention addresses this and other objects.

In one embodiment, the invention is directed to a stent retention element adapted for incorporation onto a first end of an elongate stent, and having an elastic member adapted to coil toward a second end of the elongate stent. In another embodiment, the stent retention element includes an elongate section adapted to extend axially from the first end of the elongate stent. According to another embodiment, the elastic member is adapted to coil toward the second end of the elongate stent at distances around the elongate section of the stent retention element. In an alternative embodiment, the elastic member is adapted to coil toward the second end of the elongate stent at distances around a first section of the elongate stent.

According to one embodiment, the distances at which the elastic member is adapted to coil are substantially constant to form the elastic member as a substantially cylindrical helix having a plurality of coils with substantially equal diameters. According to an alternative embodiment, the distances at which the elastic member is adapted to coil varies to form the elastic member as a conical spiral having a plurality of coils, each of the plurality of coils having an associated diameter, and the associated diameter increasing as the coils extend toward the second end of the elongate stent.

According to one embodiment, the elastic member is adapted for anchoring the first end of the elongate stent in a human urinary bladder. According to an alternative embodiment, the elastic member is adapted for anchoring the first end of the elongate stent in a human kidney. According to one feature, the elastic member is formed to compress from a steady state in response to an axial force directed from the second end of the elongate stent toward the first end of the elongate stent. In one aspect, compression of the elastic member effectively retracts a portion of the elongate section of the stent retention element and/or a portion of the elongate stent into the kidney or urinary bladder to accommodate ureter shortening. According to another feature, the elastic member is formed to return to an uncompressed steady state in response to removal of the axial force, thus re-extending the previously retracted portion of the elongate section of the stent retention element or elongate stent back into the ureter.

According to a further feature, the elastic member is formed to expand from a steady state in response to an axial force directed from the first end of the elongate stent toward the second end of the elongate stent to effectively extend a portion of the elongate stent and/or a portion of the elongate section of the stent retention element further into the ureter to accommodate ureter lengthening. According to another feature, the elastic member is formed to return to an unextended steady state in response to removal of the axial force, thus retracting the previously extended portion of the elongate section of the stent retention element or elongate stent back out of the ureter. In one embodiment, the elastic member is formed to provide a compressive stroke of at least about 5 cm.

According to another feature of the invention, those of the plurality of coils that have a relatively smaller diameter are adapted to pass through each of the plurality of coils having a relatively larger diameter in response to an axial force directed from the first end toward the second end of the elongate stent. According to another feature, the elastic member is adapted to return to an initial steady state in response to removal of the axial force.

In one embodiment, the elastic member is formed to be hollow and defines a retention element lumen. According to an alternative embodiment, the retention element is formed to be substantially solid. According to one feature, the elastic member is adapted to uncoil in response to a catheter body being extended over the retention element and/or a guide wire being inserted into the retention element lumen. According to another feature, the elastic member is formed from a super elastic material.

In another embodiment, the invention is directed to a stent having an elongate body and a first retention element. The elongate body has first and second ends and defines an internal lumen extending there between. It also has a length at least sufficient to extend through an anatomical lumen of a patient from a first anatomical site to a second anatomical site. In one embodiment, the first retention element is adapted for anchoring the stent at the first anatomical site and includes a first elastic member coiling toward the second end of the elongate body. According to a further embodiment, the first elastic member coils toward the second end of the elongate body at first distances around a first section of the elongate body. In an alternative embodiment, the first retention element includes a first elongate section extending axially from the first end of the elongate body. According to a feature of this embodiment, the first elastic member coils toward the second end of the elongate body at first distances around the first elongate section of the first retention element.

According to a further embodiment, the stent also includes a second retention element adapted for anchoring the stent at the second anatomical site. According to one embodiment, the second retention element includes a second elastic member coiling toward the first end of the elongate body. According to a further embodiment, the second elastic member coils toward the first end of the elongate body at second distances around a second section of the elongate body. In an alternative embodiment, the second retention element includes a second elongate section extending axially from the second end of the elongate body. According to a feature of this embodiment, the second elastic member coils toward the first end of the elongate body at second distances around the second elongate section of the second retention element.

According to one embodiment, the first and second distances at which the first and second elastic members coil is substantially constant to form the elastic members as substantially cylindrical helixes having a plurality of coils with substantially equal diameters. According to an alternative embodiment, the first and second distances at which the elastic members coil varies to form the elastic members as a conical spiral having a plurality of coils, each of the plurality of coils having an associated diameter that increases as the first elastic member coils toward the second end of the elongate body and the second elastic member coils toward the first end of the elongate body.

According one embodiment, the anatomical lumen is a ureter, the first anatomical site is a kidney and the second anatomical site is a urinary bladder. According to a further embodiment, the first retention element is adapted for insertion into the kidney and the second retention element is adapted for insertion into the urinary bladder.

According to one feature, at least one of the first and second retention elements is adapted to compress to retract a portion of the first or second sections of the elongate body or a portion of the elongate section of the first or second retention elements from the ureter to accommodate ureter shortening.

According to another feature, at least that retention element is adapted to decompress, thereby re-extending the retracted portion of the elongate body or retention element back into the ureter to accommodate re-lengthening. According to an additional feature, at least one of the first and second retention elements is adapted to expand, thereby extending a portion of the first or second sections of the elongate body or a portion of the elongate section of the first or second retention elements into the ureter to accommodate ureter lengthening.

According to another embodiment, the invention is directed to a method of placing a stent in a patient. The method includes the step of providing a stent having: an elongate body having first and second ends and defining an internal lumen extending there between, and having a length sufficient to extend through an anatomical lumen of a patient from a first anatomical site to a second anatomical site; and a retention element axially extending from the first end toward the second end of the elongate body while coiling at a first distance around a first section of the elongate body. The method further includes, inserting the stent into the anatomical lumen of the patient; and positioning the stent in the patient with the first retention element at the first anatomical site.

According to one embodiment, the first anatomical site is a urinary bladder and the positioning step includes, positioning the retention element substantially within the urinary bladder to anchor the first end of the elongate body to the urinary bladder. According to another embodiment, the first anatomical site is a kidney and the positioning step includes, positioning the retention element substantially within the kidney to anchor the first end of the elongate body to the kidney.

According to a further embodiment, the invention is directed to a method of removing a stent from a patient. The stent includes an elongate body with first and second ends and defining an internal lumen extending there between, and extending through an anatomical lumen of a patient from a first anatomical site to a second anatomical site. The stent also includes a retention element incorporated with the first end of the elongate body and coiling toward the second end of the elongate body to anchor the first end of the elongate body at the first anatomical site. The method includes the steps of releasing the retention element from the first anatomical site and removing the stent from the anatomical lumen of the patient. According to one embodiment of this method, the first anatomical site is a urinary bladder and the releasing step includes releasing the retention element from the urinary bladder. According to another embodiment of this method, the first anatomical site is a kidney and the releasing step includes releasing the retention element from the kidney.

BRIEF DESCRIPTION OF THE DRAWINGS

The foregoing and other objects of the invention and the various features thereof may be more fully understood from the following description when read together with the accompanying drawings in which like-reference designations generally refer to the same parts throughout the different views and in which the depicted components are not necessarily drawn to scale.

DESCRIPTION OF AN ILLUSTRATIVE EMBODIMENT

As described above in summary, the invention relates generally to stents. More particularly, in one embodiment, the invention is directed to a stent retention element. In further embodiments, the invention is directed to a ureteral stent having a retention element adapted to accommodate both ureter lengthening and shortening, while reducing patient discomfort and inhibiting stent migration.

Figure 1:
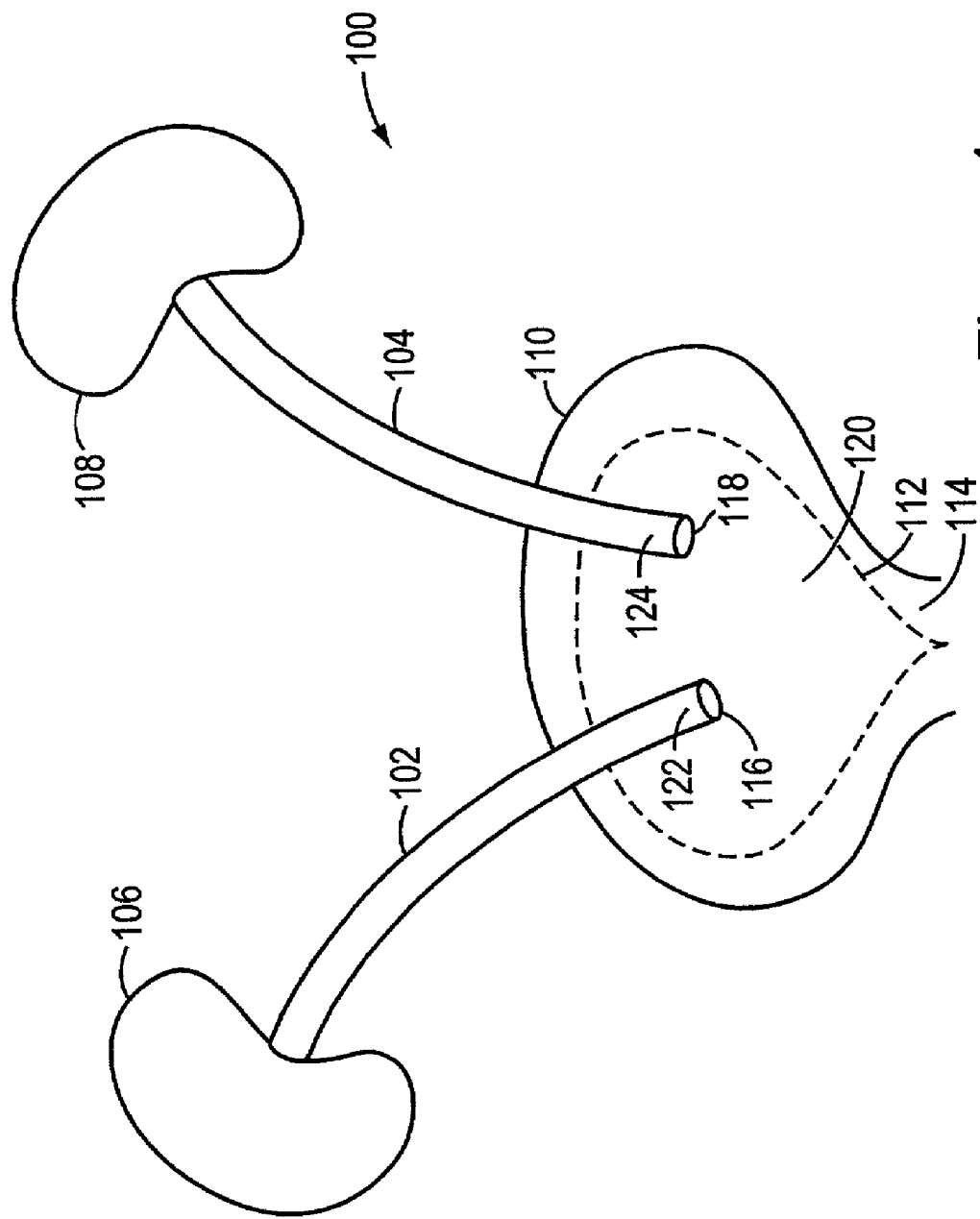
FIG. 1 is a conceptual background diagram depicting a human urinary tract.
Figure 2A:
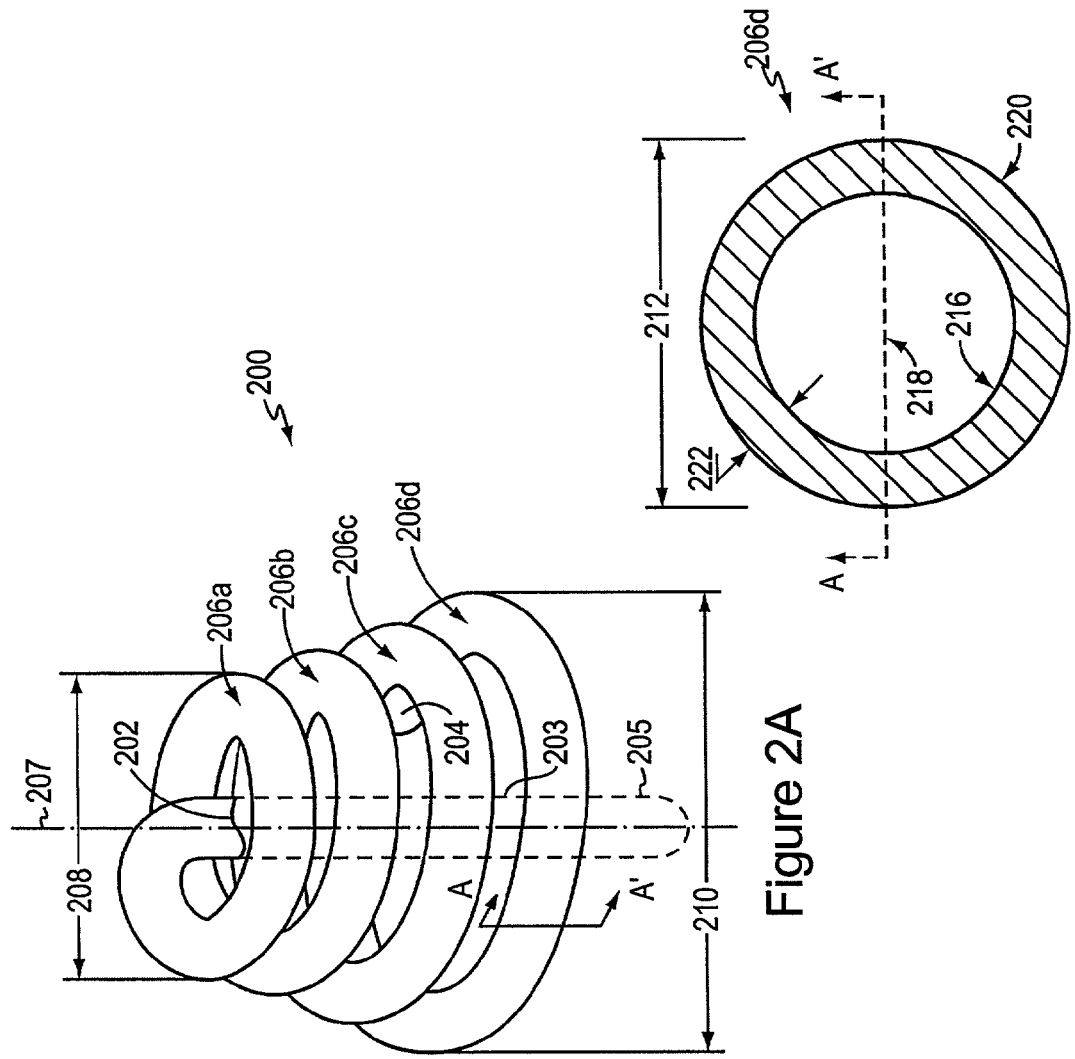
FIG. 2A is a perspective, side view of a stent retention element according to an illustrative embodiment of the invention.

FIG. 2A is a side perspective view of a retention element 200 according to an illustrative embodiment of the invention. The retention element 200 includes an elastic member 206 and optionally, an elongate section 203. The elastic member 206 includes a plurality of coils 206a-206d coiling at a distance around a substantially central axis 207 from a first end 202 of the elastic member 206 to a second end 204 of the elastic member 206. Illustratively, the coils 206a-206d are formed, at least in part, from an elastic or super elastic material having shape retention features to enable the retention element 200 to return to a coiled shape after being substantially straightened during transitory stages of insertion and removal, and after being expanded or compressed while inside a patient. The shape retention features also enable various patient comfort aspects discussed in more detail below with respect to FIGS. 3A-3C.

Appropriate shape retention materials for the coils 206a-206d includes, for example, alloys of In—Ti, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, Fe$_3$Be, Fe$_3$Pt, Ni—Ti—V, Fe—Ni—Ti—Co, and Cu—Sn, along with any other shape retaining materials. According to one illustrative embodiment, the super elastic material is a nickel and titanium alloy, known by the tradename Nitinol®, available from Memry Corp. of Brookfield, Conn. and SMA, Inc. of San Jose, Calif. The ratio of nickel and titanium in Nitinol® can vary. In one preferred embodiment, the material of the retention element 200 has a nickel-to-titanium ratio of about 50% to about 56% nickel by weight.

Figure 3A:
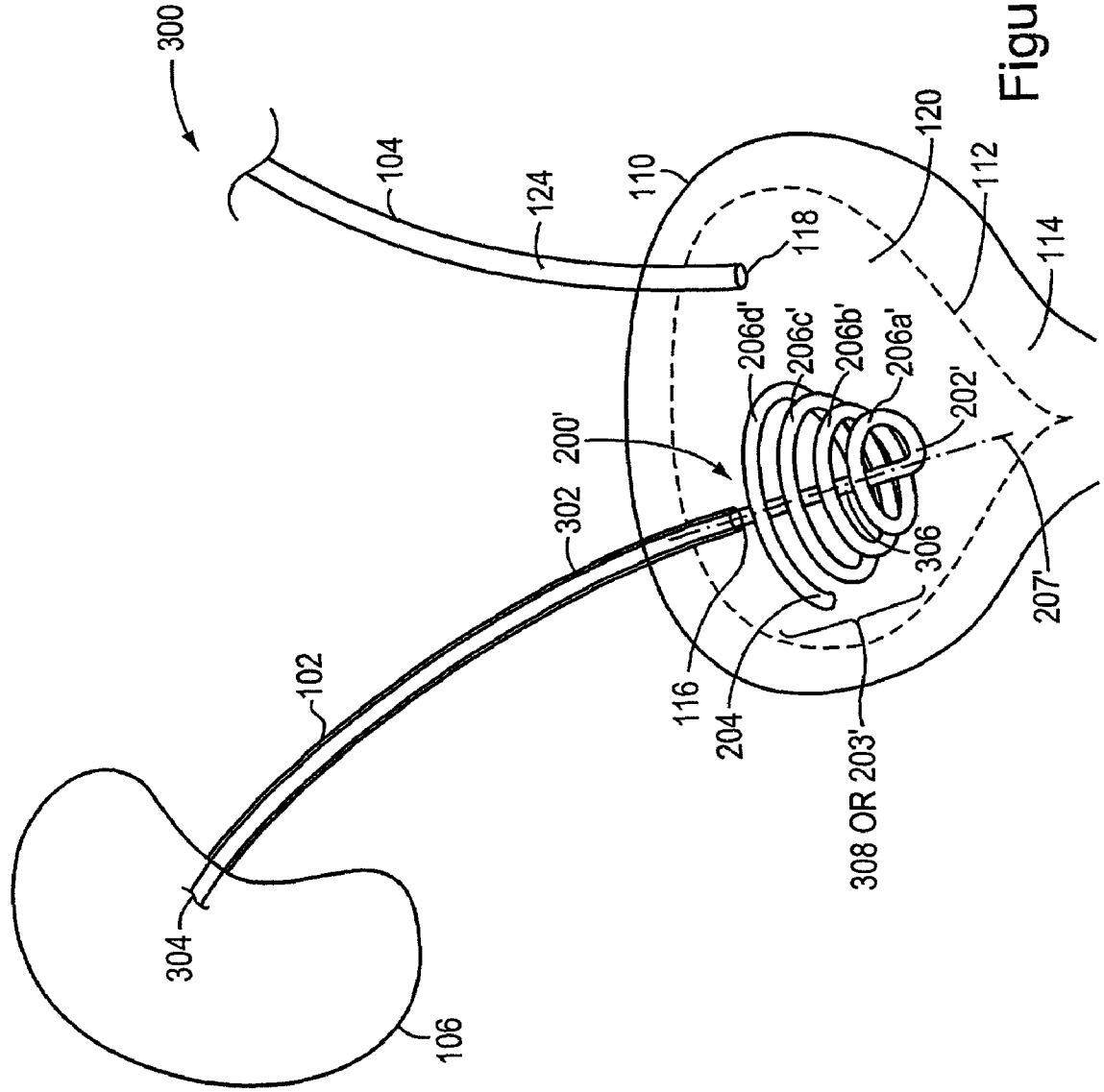
FIG. 3A is a conceptual diagram depicting a stent employing the retention element of FIG. 2A to anchor one end of the stent in a patient's urinary bladder according to an illustrative embodiment of the invention.

Referring briefly to FIG. 3A, the elastic member 206 is adapted to coil from a first end 306 of a stent 302 toward a second end 304 of the stent 302 at distances around a first section 308 of the stent 302. As shown in FIG. 2A, optionally, the retention element 200 includes an elongate section 203 adapted to extend axially from a stent end 304 or 306. In such an embodiment, the elastic member 206 is adapted to coil toward the second end 304 of the stent 302 at distances around the elongate section 203 of the retention element 200.

In one embodiment, the distances at which the elastic member 206 is adapted to coil about the stent section 308 or the elongate section 203 of the retention element 200 are substantially constant to form the elastic member 206 as a substantially cylindrical helix having a plurality of coils 206a-206d with substantially equal diameters.

However, according to the illustrative embodiment of FIG. 2A the distances at which the coils 206a-206d coil around the stent section 308 or the elongate section 203 varies to form the elastic member 206 as a conical spiral having a plurality of coils 206a-206d, each having an associated diameter, and the associated diameter increasing from a minimum diameter 208 for coil 206a to a maximum diameter 210 for coil 206d as the retention element extends toward the second end 304 of the stent 302.

Figure 2C:
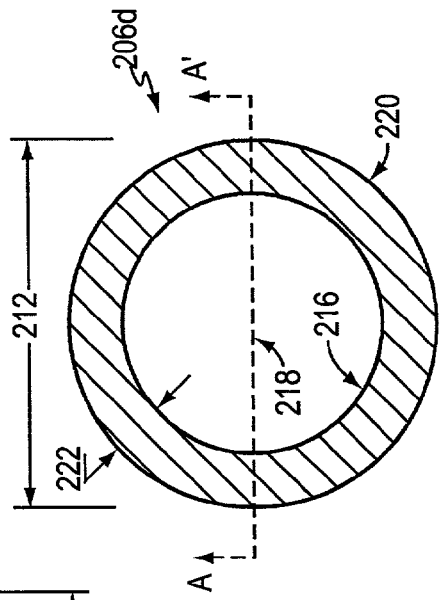
FIG. 2C is a cross-sectional view, taken along view AA', depicting a substantially hollow stent retention element according to an alternative illustrative embodiment of the invention.
Figure 2B:
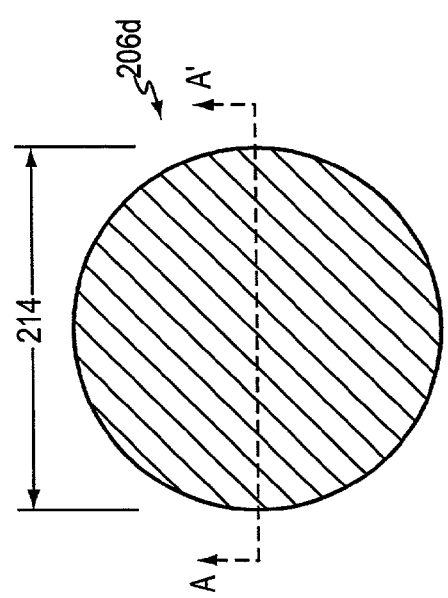
FIG. 2B is a cross-sectional view, taken along view AA', depicting a substantially solid stent retention element according to an illustrative embodiment of the invention.

FIG. 2B is a cross-sectional view of the coil 206d taken along view AA'. As depicted in FIG. 2B, according to the illustrative embodiment, the coils 206a-206d are formed to be substantially solid. In the embodiment of FIG. 2B, each coil 206a-206d is formed to have a substantially ellipsoid cross-section AA'. More particularly, in the illustrative embodiment, each coil 206a-206d has a substantially circular cross-section AA', with an outside diameter 214 between about 0.052 inches and 0.13 inches. However according to alternative embodiments, other cross-sectional shapes may be employed.

FIG. 2C is a cross-sectional view of the coil 206d taken along view AA' according to an alternative illustrative embodiment. In the alternative embodiment of FIG. 2C, the coils 206a-206d are formed as a hollow tube having an inner wall 216 and an outer wall 220. In the illustrative embodiment of FIG. 2C, coil 206d has an outside diameter 212 between about 0.5 inches and about 1.0 inches and a wall thickness 222 of at least about 0.005 inches to about 0.030 inches. In the embodiment of FIG. 2C, the inner wall 216 defines an internal lumen 218 within which a guide wire may be inserted to straighten the coils 206a-206d during intermediate stages of insertion and removal. Although the illustrative embodiments of FIGS. 2B and 2C depict the retention element 200 as being formed from a material having a substantially uniformly shaped cross-section throughout, in other embodiments, such cross-sectional shape may vary. By way of example, a cross-section taken at end 202 may be less than or greater than a cross-section taken at end 204.

In the following descriptions of FIGS. 3A-3C, the use of a "prime" or "double prime" symbol indicates correspondence between elements of FIG. 2A and like numbered elements of FIGS. 3A-3C.

FIG. 3A is a conceptual diagram 300 depicting a retention element 200', of the type shown in FIG. 2A, incorporated onto the bladder end 306 of a stent 302, placed inside the human urinary tract 100. The retention element 200' has an end 202' attached to the bladder end 306 of the stent 302. The section 308 of the stent 302 extends into the bladder 110 substantially along the axis 207'. As attached to the stent 302, the retention element 200' is located in the urinary bladder 110 and extends from the bladder end 306 of the stent 302 toward the kidney end 304 of the stent 302 while the coils 206a'-206d' coil at a distance around the stent section 308.

The retention element 200' may be attached to the bladder end 306 by any appropriate means. Alternatively, the retention element 200' may be formed integrally with the bladder end 306. As mentioned above, in other alternative embodiments, the elongate section 203 may substitute for section 308 and be formed as part of the retention element 200' as opposed to part of the stent 302.

According to one illustrative embodiment, the stent 302 is sized to be an appropriate length to extend through the ureter 102 between the kidney 106 and the urinary bladder 110 during a nominal at-rest patient state. As mentioned above with respect to FIG. 2A and as described in further detail below with respect to FIGS. 4A and 4B, in response to the ureter 102 lengthening from the nominal state for any reason, the coils 206a'-206d' compress to allow enough of section 308 to extend into the ureter 102 to accommodate the ureter 102 lengthening. Subsequently, in response to ureter 102 shortening, the coils 206a'-206d' decompress to retract enough of the stent section 308 back into the urinary bladder 110 to accommodate the shortening.

According to another illustrative embodiment, the stent 302 is sized to have a length too short to span the distance through the ureter 102 from the kidney 106 to the urinary bladder 110, to cause the coils 206a'-206d' to remain somewhat compressed upon insertion into the urinary bladder 110. In such a state, the coils 206a'-206d' are able to accommodate both ureter 102 shortening and ureter 102 lengthening. By way of example, if the coils 206a'-206d' are formed to have a compressive stroke of at least about 5 cm, and the stent is sized such that upon insertion the coils 206a'-206d' are compressed to about 2.5 cm of such stroke, the stent retention element 200' is able to accommodate about a 2.5 cm of ureter 102 lengthening or shortening. According to other illustrative embodiments, the coils 206a'-206d' may employ other compressive strokes without deviating from the scope of the invention.

Figure 3B:
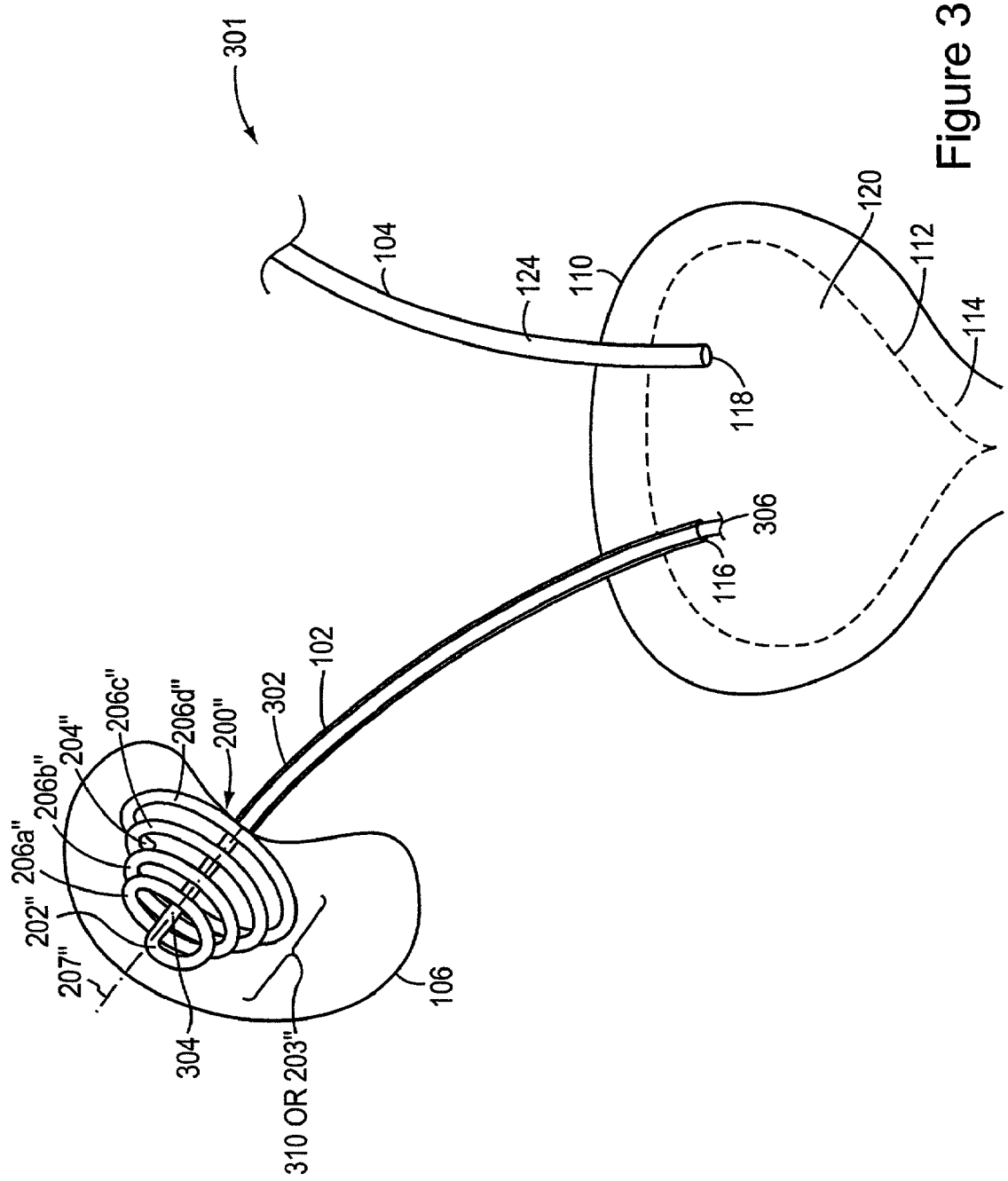
FIG. 3B is a conceptual diagram depicting a stent employing the retention element of FIG. 2A to anchor one end of the stent in a patient's kidney according to an illustrative embodiment of the invention.

FIG. 3B is a conceptual diagram 301 depicting a retention element 200", of the type shown in FIG. 2A, attached to the kidney end 304 of the stent 302, placed inside the human urinary tract 100. The retention element 200" is substantially identical to the retention element 200'. However, according to the illustrative embodiment, the retention elements 200' and 200" may be sized to accommodate the size of the anatomical site at which the retention element (200', 200") operates. The retention element 200" has an end 202" attached to the kidney end 304 of the stent 302. The section 310 of the stent 302 extends into the kidney 106 substantially along the axis 207". Thus, as attached to the stent 302, the retention element 200" extends from the kidney end 304 of the stent 302 toward the bladder end 306 of the stent 302 while the coils 206a"-206d" coil at a distance around the section 310.

As in the case of the retention element 200' of FIG. 3A, the retention element 200" may be attached or formed to the kidney end 304 of the stent 302 by any appropriate means. Also, as in the case of section 308, the section 310 may be formed as either part of the stent 302 or part of the retention element 200".

In one illustrative embodiment, the stent 302 is sized to be an appropriate length to extend through the ureter 102 between the urinary bladder 110 and the kidney 106 during a nominal at-rest patient state. As mentioned above with respect to FIG. 2A and as described in further detail below with respect to FIGS. 4A and 4B, in response to the ureter 102 lengthening from the nominal state for any reason, the coils 206a"-206d" compress to allow enough of the section 310 to extend into the ureter 102 to accommodate the lengthening. Subsequently, in response to ureter 102 shortening, the coils 206a"-206d" decompress to retract enough of the section 310 back into the kidney 106 to accommodate the shortening.

As in the example of FIG. 3A, the stent 302 may be sized to have a length too short to span the distance through the ureter 102 from the urinary bladder 110 to the kidney 106 to cause the coils 206a"-206d" to remain somewhat compressed upon insertion into the kidney 106. In such a state, the coils 206a"-206d" are able to compress and/or decompress to accommodate both ureter 102 shortening and ureter 102 lengthening in a similar fashion to the coils 206a'-206d' described above with respect to FIG. 3A.

Figure 3C:
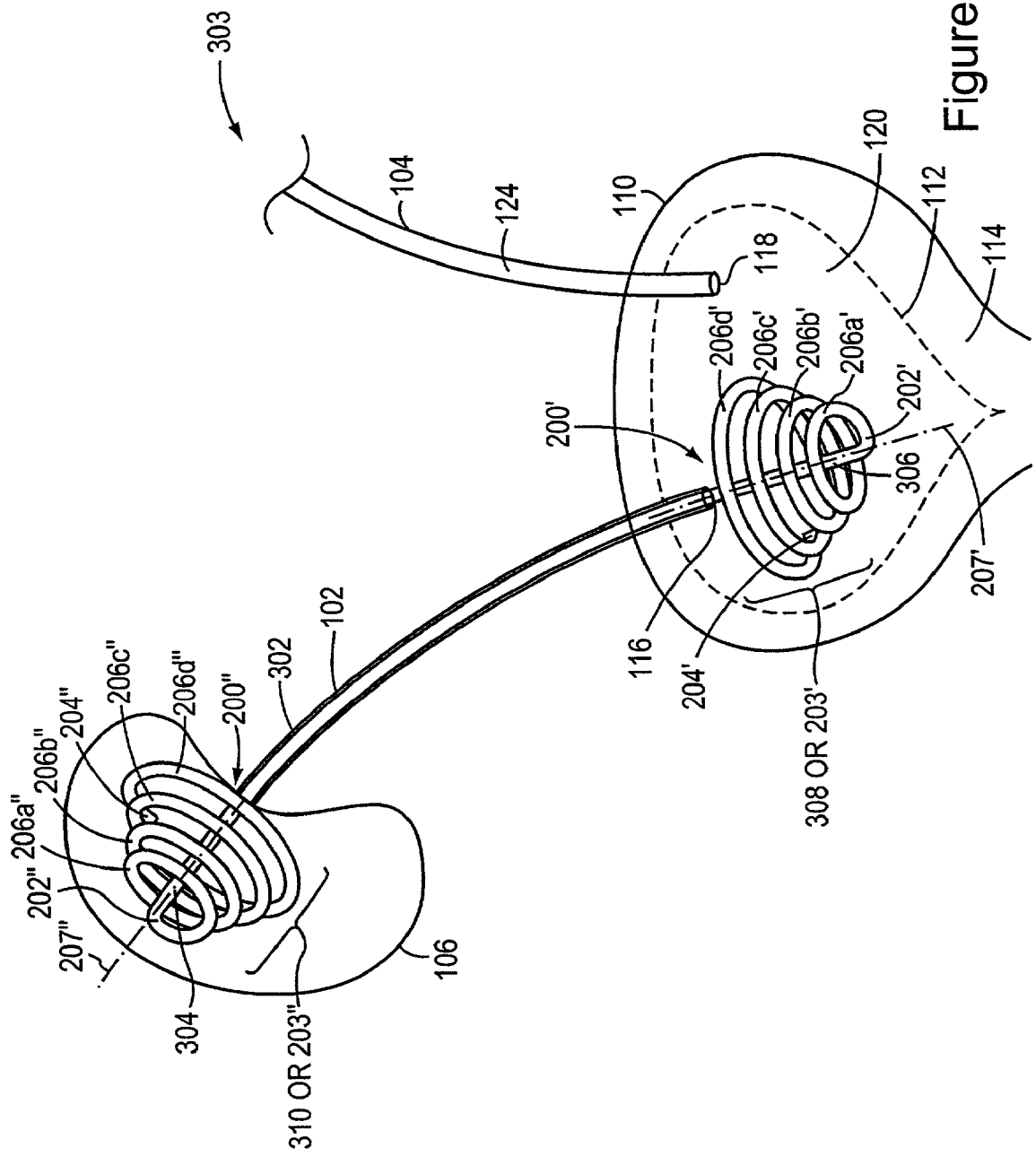
FIG. 3C is a conceptual diagram depicting a stent employing the retention element of FIG. 2A to anchor a first end of the stent in a patient's urinary bladder and a second end of the stent in a patient's kidney according to an illustrative embodiment of the invention.

FIG. 3C is a conceptual diagram 303 depicting a stent 302 having a retention element 200', of the type shown in FIG. 2A, attached to the bladder end 306 and a retention element 200", of the type shown in FIG. 2A, attached to the kidney end 304, placed inside the human urinary tract 100. The retention elements 200' and 200" operate substantially as described above with respect to FIGS. 3A and 3B. However, with the urinary bladder end 306 and the kidney end 304 employing retention elements 200' and 200", respectively, additional benefits are realized.

By way of example, as described above, the stent 302 may be sized to extend through the ureter 102 between the urinary bladder 110 and the kidney 106 during a nominal at-rest patient state. With both retention elements 200' and 200" being utilized, in response to the ureter 102 lengthening from the nominal state for any reason, both sets of coils 206a'-206d' and 206a"-206d" are available for compression to allow both sections 308 and 310 of the stent 302 to extend into the ureter 102 to accommodate for the lengthening. Similarly, in response to ureter 102 shortening, both sets of coils 206a'-206d' and 206a"-206d" are available for decompression to retract enough of sections 308 and 310 back into the urinary bladder 110 and the kidney 106, respectively, to accommodate the shortening. Thus, use of both retention elements 200' and 200" increases the amount of ureter 102 lengthening and shortening for which the stent 102 can compensate.

An additional benefit is also realized when the stent 302 is sized to have a length too short to span the distance through the ureter 102 between the urinary bladder 110 and the kidney 106. By way of example, if each set of coils 206a'-206d' and 206a"-206d" are formed to have a compressive stroke of about 5 cm, and the stent is sized such that upon insertion both sets of coils 206a'-206d' and 206a"-206d" are compressed to about 2.5 cm, the stent retention elements 200' and 200" combined can accommodate up to a 5 cm ureter 102 lengthening or shortening, twice as much as with the single retention element embodiments of FIGS. 3A and 3B.

In one embodiment, the stent 302 has drain holes. In other embodiments, the stent retention element 200 has drain holes along one or more coils 206a-206d. In some embodiments, the elongate section 203 of the stent retention element 200 contains drain holes. In some embodiments, the drain holes have a diameter of 0.030 inches. In other embodiments, the drain holes have a diameter between 0.010 inches and 0.050 inches.

Figure 4A:
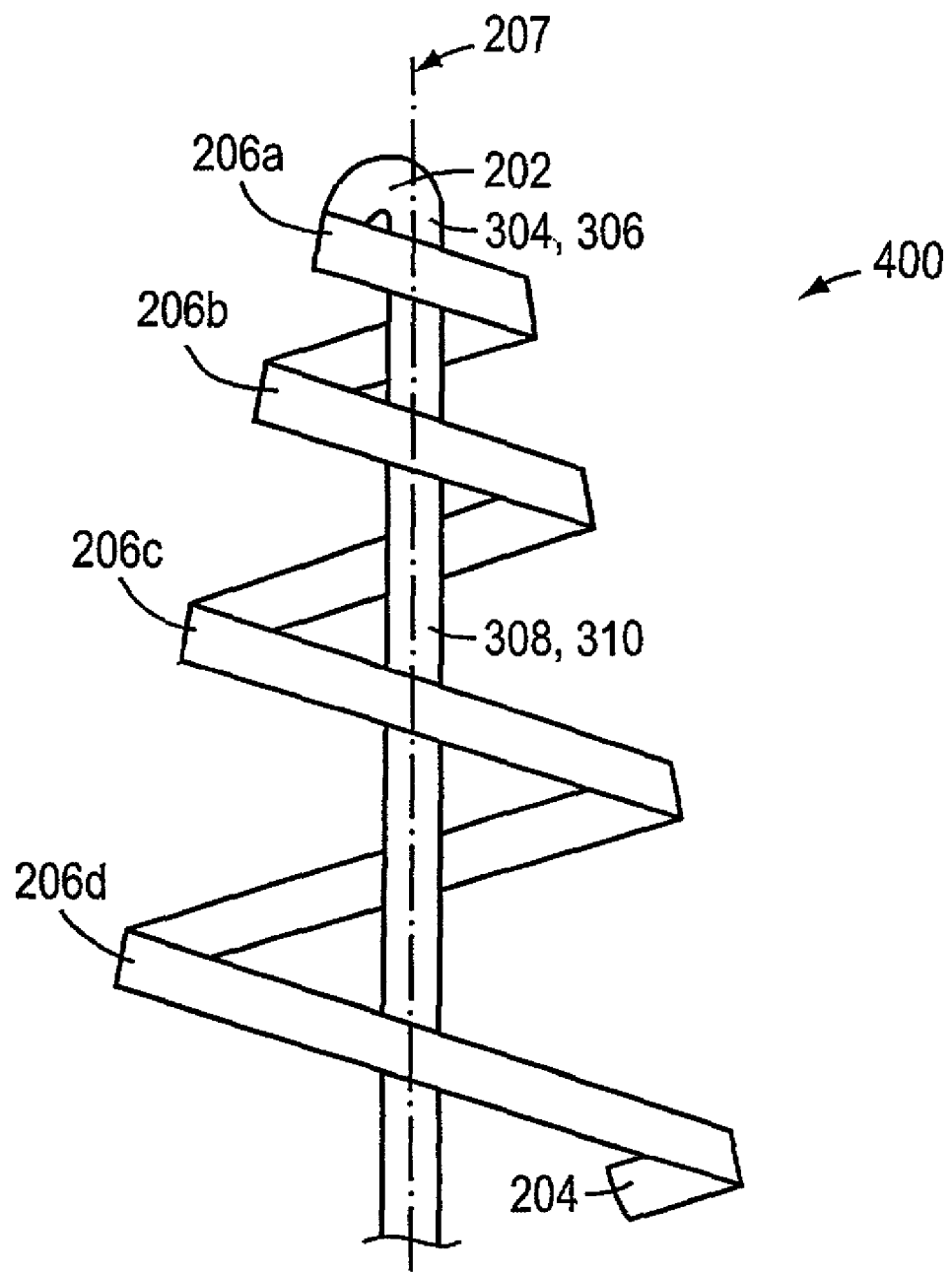
FIG. 4A is a side view of the stent retention element of FIG. 2A in a partially expanded state according to an illustrative embodiment of the invention.
Figure 4B:
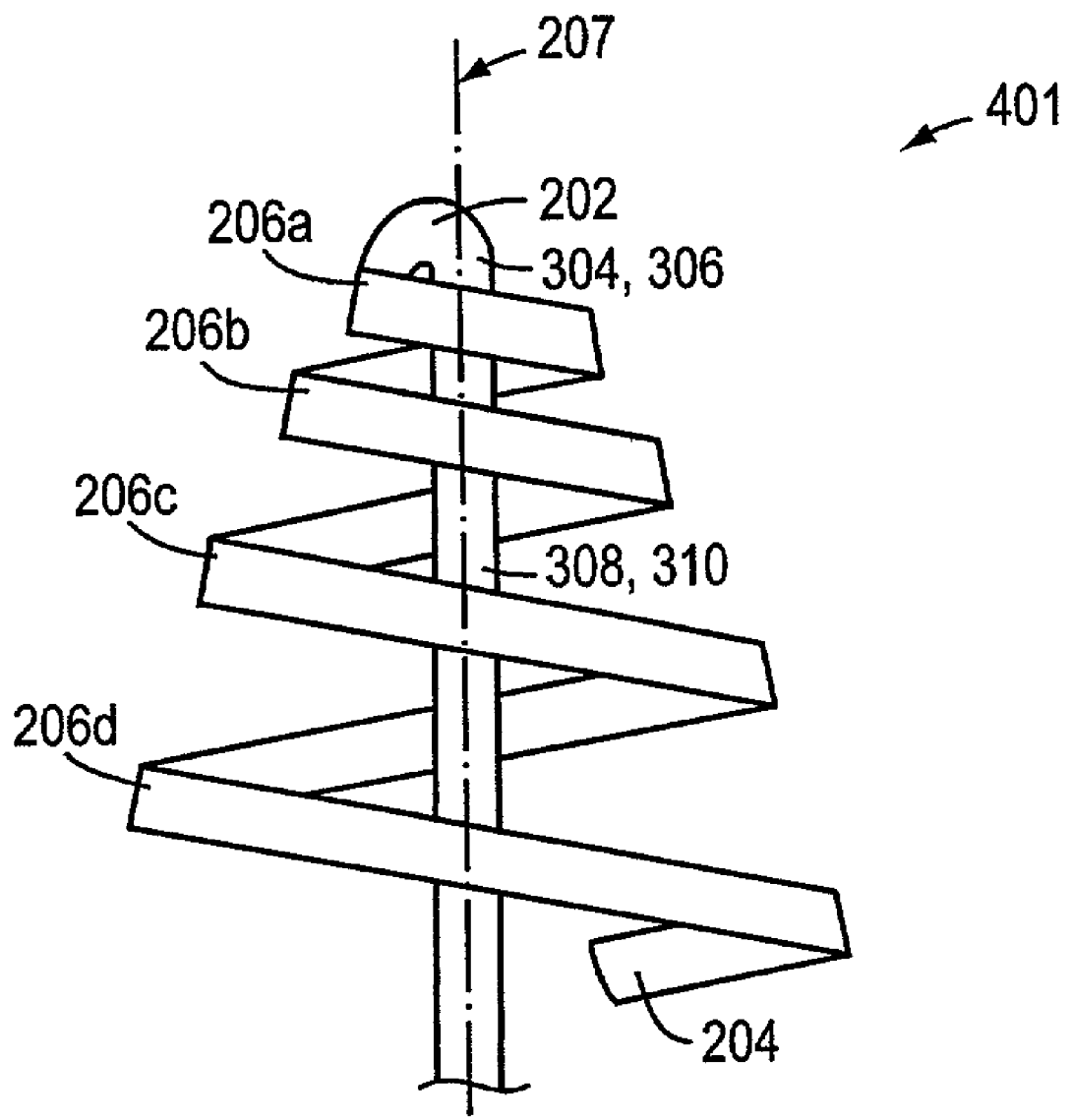
FIG. 4B is a side view of the stent retention element of FIG. 2A in a partially compressed state according to an illustrative embodiment of the invention.

FIG. 4A is a side view of the stent retention element 200 of FIG. 2A in a partially expanded state according to an illustrative embodiment of the invention. FIG. 4B is a side view of the stent retention element 200 of FIG. 2A in a partially compressed state according to an illustrative embodiment of the invention. As illustrated in FIG. 4A, the retention element 200 is adapted to expand along the axis 207 to effectively shorten the stent 302, while maintaining an anchored position, to accommodate ureter 302 lengthening during patient activity. As illustrated in FIG. 4B, the retention element 200 is also adapted to compress along the axis 207 to effectively lengthen the stent 102, in response to ureter 102 shortening during patient activity. In this way, the retention element 200 maintains the stent 302 in an anchored position while accommodating ureter 102 lengthening and shortening to reduce kidney 106 and/or bladder 110 irritation.

The cylindrical or conical spiral configuration of the coils 206*a*-206*d* of the retention element 200 performs substantially as a spring and permits compression motion. The effective spring force to compress the retention element 200 will be a function of the material Modulus of Elasticity selected, wall thickness, or diameter. According to the illustrative embodiment, the retention element 200 is capable of maximum compression and maximum decompression, as well as all intermediate positions in-between, including that of a neutral, or relaxed, state.

Figure 5B:
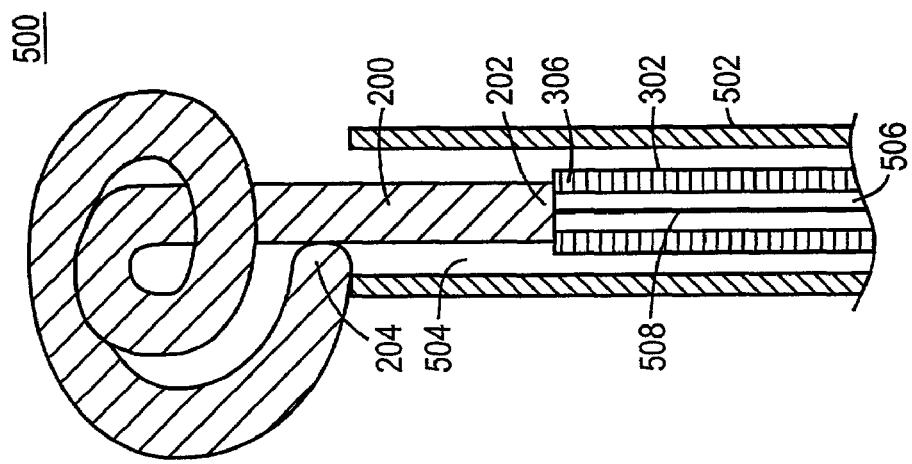
FIG. 5B is a side view, partially in cross-section, of the stent retention element of FIG. 2A coiling in response to being extended out of the catheter lumen of FIG. 5A according to an illustrative embodiment of the invention.
Figure 5A:
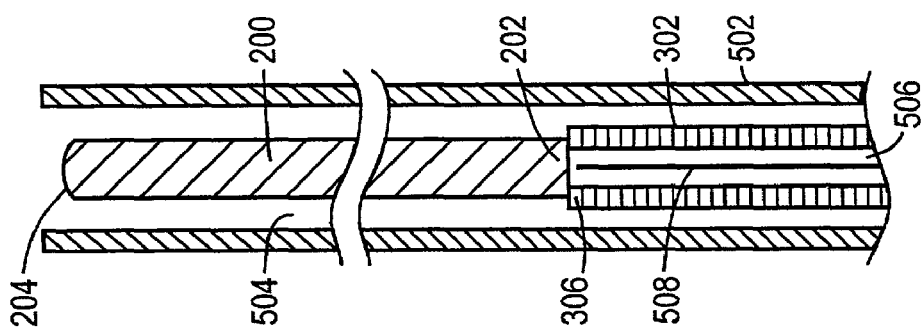
FIG. 5A is a side view, partially in cross-section, of the stent retention element of FIG. 2A uncoiled within a catheter lumen prior to insertion or subsequent to retraction according to an illustrative embodiment of the invention.

FIG. 5A is a side view, partially in cross-section, of the stent retention element 200 of FIG. 2A uncoiled within a catheter-type lumen 504 according to an illustrative embodiment of the invention. As shown during insertion, a medical operator inserts the retention element 200 through a catheter-type lumen 504, which substantially straightens coils 206*a*-206*d*. In one illustrative embodiment, a guide wire 508 is inserted into a lumen 506 of the stent 302 to push the retention element 200 through the catheter-type lumen 504 and into position. In other illustrative embodiments, other devices may be used to push the retention element 200 through the catheter-type lumen 504 and into position.

FIG. 5B is a side view, partially in cross-section, of the stent retention element 200 of FIG. 2A coiling in response to being extended out of the catheter-type lumen 504 according to an illustrative embodiment of the invention. As shown, due to its shape retention features, the retention element 200 returns to its coiled configuration as it emerges from the lumen 504.

Figure 5C:
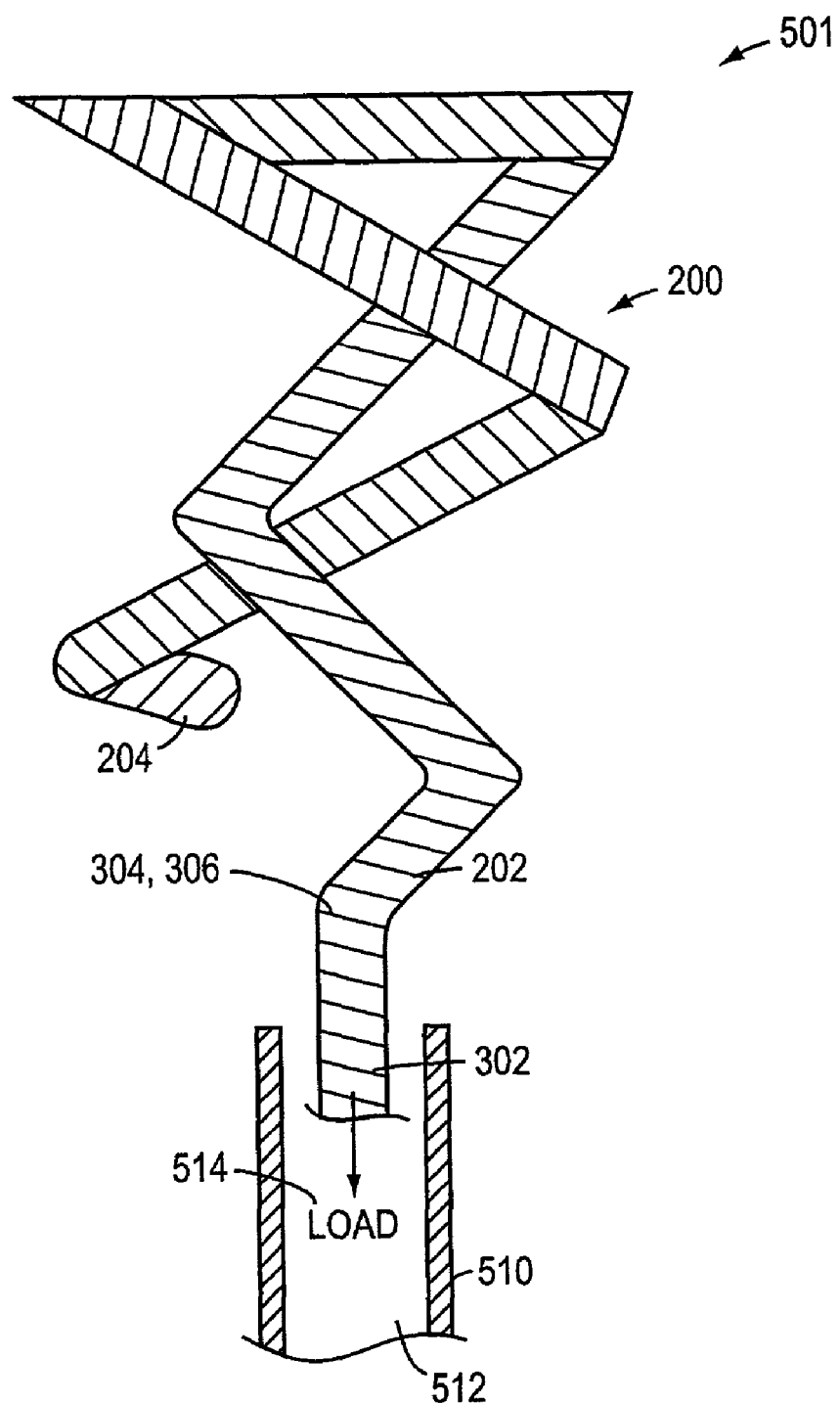
FIG. 5C is a side view, partially in cross-section, of the stent retention element of FIG. 2A uncoiling as it retracts into a catheter lumen during removal according to an illustrative embodiment of the invention.

FIG. 5C is a side view, partially in cross-section, of the stent retention element 200 of FIG. 2A uncoiling as it is retracted into a catheter-type lumen 510 during removal from a patient, according to an illustrative embodiment of the invention.

According to the illustrative embodiment of the invention, a medical operator inserts a catheter-type lumen 512 over the stent 302 and applies an axial load 514 to the retention element end 202. In response, the stent retention element 200 progressively uncoils, such that those of the plurality of coils 206*a*-206*d* having a relatively smaller diameter pass through each of the plurality of coils 206*a*-206*d* having a relatively larger diameter. Although the retention element 200 is forced to uncoil into the lumen 512, the shape retention features of the retention element 200 enable the retention element 200 to return to its neutral, or relaxed, coiled state upon removal of the axial load 514 and release from the lumen 512. It should be noted that in the optional embodiment of FIG. 2A, with the elongate section 203, a similar removal process may be followed.

The insertion and removal process depicted in FIGS. 5A through 5C function comparably whether the retention element 200' is placed in the urinary bladder 110, or the retention element 200" is placed in the kidney 106, or both.

Variations, modifications, and other implementations of what is described herein will occur to those of ordinary skill in the art without departing from the spirit and the scope of the invention. This invention is not limited to the preceding illustrative description.

What is claimed is:

1. A ureteral stent comprising,
an elongate body having a first end and a second end and defining an internal lumen extending there between, the elongate body having a length at least sufficient to extend through a ureter of a patient such that the first end is configured to be disposed in a bladder of the patient and the second end is configured to be disposed in a kidney of the patient;
a first retention element incorporated with the first end of the elongate body, the first retention element having a plurality of coils coiling toward the second end of the elongate body around a first section of the elongate body, each of the coils from the plurality of coils coiling around the elongate body at varying distances from the first section of the elongate body and having a diameter, the diameter of each coil from the plurality of coils increasing as the plurality of coils extends from the first end toward the second end of the elongate body such that a first coil from the plurality of coils having a greater diameter than the remaining coils contacts a bladder wall of the patient when the first end of the elongate body is disposed in the bladder; and
a second coil from the plurality of coils having a diameter smaller than the remaining coils is configured to pass through at least another coil from the plurality of coils different than the first coil when at least a portion of the first section of the elongate body is moved toward the kidney during ureter lengthening when the first end of the elongate body is disposed in the bladder.

2. The stent of claim 1, further comprising:
a second retention element incorporated with the second end of the elongate body, the second retention element includes a plurality of coils that coil toward the first end of the elongate body at distances around a second section of the elongate body.

3. The stent of claim 2, wherein the distances around the second section of the elongate body are substantially constant to form the second retention element as a substantially cylindrical helix, the plurality of coils of the second retention element having substantially equal diameters.

4. The stent of claim 2, wherein the distances around the second section of the elongate body vary to form the second retention element as a conical spiral, the plurality of coils of the second retention element each having a diameter, the diameter increasing as the plurality of coils of the second retention element extends from the second end toward the first end of the elongate body.

5. The stent of claim 4, wherein coils from the plurality of coils of the second retention element having a smaller diameter are adapted to pass through coils from the plurality of coils of the second retention element having a larger diameter.

6. The ureteral stent of claim 2, wherein the elongate body defines a length between the first end and the second end of the elongate body, the length of the elongate body being constant when the first retention element and the second retention element move with respect to each other in response to bodily movement.

7. The ureteral stent of claim 2, wherein the elongate body, the first retention element and the second retention element are formed with a tubing having a wall thickness between about 0.005 inches and 0.030 inches.

8. The ureteral stent of claim 2, wherein the elongate body, the first retention element and the second retention element are formed with an elongate member having an outer diameter between about 0.052 inches and 0.13 inches.

9. The ureteral stent of claim 2, wherein the first retention element and the second retention element each have a compressive stroke of up to 2.5 cm to accommodate ureter lengthening and shortening.

10. The stent of claim 1, wherein the first retention element defines an internal retention element lumen.

11. The stent of claim 10, wherein the first retention element is adapted to uncoil in response to inserting a guide wire into the internal retention element lumen.

12. The stent of claim 1, wherein the plurality of coils of the first retention element coil about an axis, the axis being substantially coaxial with an axis defined by the elongate body.

13. The stent of claim 1, further comprising:
a second retention element incorporated with the second end of the elongate body,
the first retention element and the second retention element are configured to be movable with respect to each other in response to lengthening and shortening of the ureter.

14. The ureteral stent of claim 1, further comprising:
a second retention element, the second retention element includes a first coil and a second coil, the first coil of the second retention element being larger than the second coil of the second retention element and being configured to contact a wall of the kidney of the patient to help retain at least a portion of the elongate body within the kidney of the patient.

15. The ureteral stent of claim 1, wherein the first retention element has a first end adjacent the first end of the elongate body and a second end disposed between the first end of the elongate body and the second end of the elongate body, a distance between the first end of the first retention element and the second end of the first retention element being configured to vary in response to bodily movement of the patient.

16. The ureteral stent of claim 1, wherein the first retention element is monolithically formed with the elongate body.

17. The ureteral stent of claim 1, wherein the first retention element has a compressive stroke of up to 2.5 cm to accommodate ureter lengthening and shortening.

18. The ureteral stent of claim 1, wherein the first retention element is formed with nickel titanium alloy has a nickel-to-titanium ratio of about 50% to about 56% nickel by weight.

19. The ureteral stent of claim 1, wherein the first end of the elongate body terminates at the second coil.

20. The ureteral stent of claim 1, wherein the first retention element is configured to compress and expand over the first section of the elongate body to accommodate ureter lengthening and shortening when the first retention element is disposed within the bladder of the patient.

21. A ureteral stent, comprising:
an elongate body; and
an elastic member disposed at a first end of the elongate body, the elastic member including a plurality of coils adapted to coil around a first end portion of the elongate body and toward a second end of the elongate body, each of the coils from the plurality of coils having a diameter around the first end portion of the elongate body, a first coil from the plurality of coils being disposed at a first end of the elastic member and closer to the first end of the elongate body than the remaining coils, the first coil having a diameter smaller than the remaining coils from the plurality of coils; and
a second coil from the plurality of coils being disposed at a second end of the elastic member and closer to the second end of the elongate body than the remaining coils, the second coil having a diameter greater than the remaining coils from the plurality of coils,
the first coil from the plurality of coils configured to pass through at least another coil from the plurality of coils different than the second coil from the plurality of coils when at least a portion of the first end portion of the elongate body is moved in a direction toward the second end of the elongate body during ureter lengthening when the elastic member is disposed in one of the bladder or the kidney of a patient.

22. The ureteral stent of claim 21, wherein the diameter of each coil from the plurality of coils increases as the plurality of coils extend toward the second end of the elongate body to form the elastic member as a conical spiral.

23. The ureteral stent of claim 21, wherein the elastic member defines a lumen.

24. The ureteral stent of claim 21, wherein a distance between the first end and the second end of the elastic member is configured to vary in response to lengthening and shortening of the ureter.

25. The ureteral stent of claim 21, wherein the plurality of coils coil about an axis, the axis being substantially coaxial with an axis defined by the elongate body.

26. The ureteral stent of claim 21, wherein the second coil of the elastic member is configured to contact a wall of the kidney of the patient to help retain at least a portion of the elongate body within the kidney of the patient.

27. The ureteral stent of claim 21, wherein the second coil of the elastic member is configured to contact a wall of the bladder of the patient to help retain at least a portion of the elongate body within the bladder of the patient.

28. The ureteral stent of claim 21, wherein the elongate body has an outer diameter between about 0.052 inches and 0.13 inches.

29. The ureteral stent of claim 21, wherein the elastic member is formed with a tubing having an outer diameter between about 0.052 inches and 0.13 inches.

30. The ureteral stent of claim 21, wherein the elastic member can vary in length in response to bodily movement of a patient up to a stroke of at least 2.5 cm when the elastic member is disposed in one of a bladder or kidney of the patient.

31. The ureteral stent of claim 21, wherein the first end portion of the elongate body terminates at the first coil.

32. The ureteral stent of claim 21, wherein the elastic member is configured to compress and expand over the first end portion of the elongate body to accommodate ureter lengthening and shortening when the elastic member is disposed within the bladder or the kidney of the patient.

33. A ureteral stent comprising,
an elongate body having a first end and a second end and defining an internal lumen between the first end and the second end of the elongate body, the elongate body having a length defined by the first end and the second end of the elongate body, the first end of the elongate body configured to be disposed in a kidney of the patient and the second end of the elongate body configured to be disposed in a bladder of the patient;
a first retention element monolithically formed with the first end of the elongate body, the first retention element having a plurality of coils coiling toward the second end of the elongate body around a first section of the elongate body, and configured to help anchor the stent in the ureter of the patient; and a second retention element monolithically formed with the second end of the elongate body, the second retention element coiling toward the first end of the elongate body and configured to help anchor the stent in the ureter of the patient, the plurality of coils of the first retention element including a first coil and a second coil, the second coil of the first retention element being closer to the second end of the elongate body than the first coil of the first retention element, the first coil of the first retention element having a smaller diameter than a diameter of the remaining coils from the plurality of coils of the first retention element, the plurality of coils of the second retention element including a first coil and a second coil, the second coil of the second retention element being closer to the first end of the elongate body than the first coil of the second retention element, the first coil of the second retention element having a smaller diameter than a diameter of the remaining coils from the plurality of coils of the second retention element, the first coil of the first retention element configured to pass through at least another coil from the plurality of coils of the first retention element different than the second coil of the first retention element at substantially the same time as the first coil of the second retention element passes through at least another coil from the plurality of coils of the second retention element different than the second coil of the second retention element as the ureter is lengthened.

34. The ureteral stent of claim 33, wherein the first retention element has a first end adjacent the first end of the elongate body and a second end disposed between the first end of the elongate body and the second end of the elongate body, the second retention element has a first end adjacent the second end of the elongate body and a second end disposed between the second end of the elongate body and the first end of the elongate body, the second end of the first retention element and the second end of the second retention element configured to move with respect to each other in response to bodily movement of the patient without changing the length of the elongate body.

35. The ureteral stent of claim 33, wherein the elongate body, the first retention element and the second retention element are formed with a material having a nickel-titanium alloy having a nickel-to-titanium ratio of about 50% to about 56% nickel by weight.

36. The ureteral stent of claim 33, wherein the first retention element and the second retention element are configured to move with respect to each other in response to bodily movement of the patient without changing the length of the elongate body, and the first retention element is configured to compress and expand over the first section of the elongate body to accommodate ureter lengthening and shortening when the first retention element is disposed within the kidney of the patient.

37. The ureteral stent of claim 33, wherein the first retention element and the second retention element each have a compressive stroke of up to 2.5 cm to accommodate ureter lengthening and shortening.

38. The ureteral stent of claim 33, wherein the first end of the elongate body terminates at the first coil of the first retention element, the second end of the elongate body terminates at the first coil of the second retention element.

* * * * *